United States Patent [19]
Beihoffer et al.

[11] Patent Number: 6,140,550
[45] Date of Patent: *Oct. 31, 2000

[54] WATER-ABSORBENT ARTICLE AND METHOD

[75] Inventors: Thomas W. Beihoffer, Arlington Heights; Anthony S. Tomlin, Island Lake, both of Ill.

[73] Assignee: BASF Aktiengesellschaft, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/884,593

[22] Filed: Jun. 27, 1997

[51] Int. Cl.$^7$ ........................................ A61F 13/15
[52] U.S. Cl. .................... 604/366; 604/365; 604/368; 604/369; 604/370; 604/372; 604/374; 604/378
[58] Field of Search ..................... 604/365, 366, 604/368, 369, 359, 360, 370, 372, 374, 378

[56] References Cited

U.S. PATENT DOCUMENTS

| | | | |
|---|---|---|---|
| 2,690,415 | 9/1954 | Shuler | 604/369 |
| 2,788,003 | 4/1957 | Morin . | |
| 3,612,055 | 10/1971 | Mesek | 601/375 |
| 3,938,522 | 2/1976 | Repke . | |
| 4,006,887 | 2/1977 | Engels | 259/9 |
| 4,010,308 | 3/1977 | Wiczer | 428/372 |
| 4,105,033 | 8/1978 | Chatterjee et al. . | |
| 4,129,132 | 12/1978 | Butterworth et al. . | |
| 4,235,237 | 11/1980 | Mesek et al. | 604/368 |
| 4,315,507 | 2/1982 | Whitehead et al. | 604/366 |
| 4,392,908 | 7/1983 | Dehnel | 427/194 |
| 4,425,126 | 1/1984 | Butterworth et al. | 604/366 |
| 4,429,001 | 1/1984 | Kolpin et al. | 428/283 |
| 4,455,187 | 6/1984 | von Blücher et al. | 156/277 |
| 4,469,746 | 9/1984 | Weisman et al. | 428/289 |
| 4,500,315 | 2/1985 | Pieniak et al. | 604/379 |
| 4,510,193 | 4/1985 | Blücher et al. | 428/196 |
| 4,584,357 | 4/1986 | Harding | 524/54.21 |
| 4,600,462 | 7/1986 | Watt | 156/278 |
| 4,685,909 | 8/1987 | Berg et al. | 604/360 |
| 4,842,593 | 6/1989 | Jordan et al. | 604/360 |
| 4,902,565 | 2/1990 | Brook | 604/369 |
| 4,906,263 | 3/1990 | von Blücher et al. | 55/316 |
| 4,981,501 | 1/1991 | von Blücher et al. | 55/316 |
| 4,983,192 | 1/1991 | von Blücher et al. | 55/387 |
| 4,992,084 | 2/1991 | von Blücher et al. | 55/316 |
| 5,230,959 | 7/1993 | Young, Sr. et al. | 428/372 |
| 5,275,154 | 1/1994 | von Blücher et al. | 128/205.27 |
| 5,277,963 | 1/1994 | von Blucher et al. | 604/368 |
| 5,300,192 | 4/1994 | Hansen et al. . | |
| 5,380,594 | 1/1995 | von Blücher et al. | 428/403 |
| 5,407,447 | 4/1995 | Kaiapasha | 604/368 |
| 5,432,000 | 7/1995 | Young, Sr. et al. | 428/372 |
| 5,536,264 | 7/1996 | Hsueh et al. | 604/388 |
| 5,763,067 | 6/1998 | Bruggemann et al. | 604/369 |

OTHER PUBLICATIONS

Bayer Corporation Product Information Brochure for Bayhydrol DLN (1 page).
Liofol Company Product Information for Tycel® 7000 (4 pages).
Liofol Company Product Information for Tycel 7212 (2 pages).

*Primary Examiner*—John G. Weiss
*Assistant Examiner*—K. M. Reichle
*Attorney, Agent, or Firm*—Marshall, O'Toole, Gerstein, Murray & Borun

[57] ABSTRACT

An absorbent article including a flexible, fibrous support structure or framework in a fixed shape or configuration having particles of a superabsorbent material adhered thereto with temperature softened outer support surfaces, or with an adhesive to maintain sufficient spacing between adjacent superabsorbent particles such that liquid can more freely enter the absorbent article for contact with the superabsorbent particles.

26 Claims, 4 Drawing Sheets

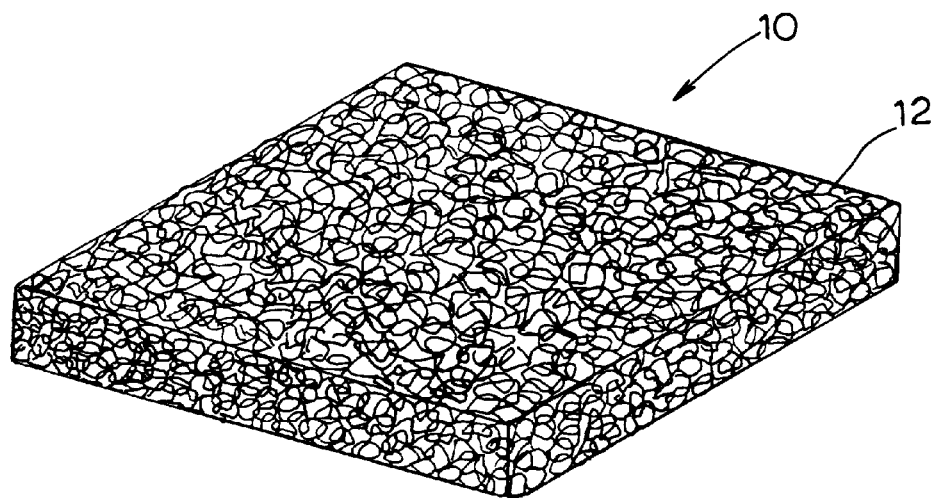
FIG. 1
FIG. 2
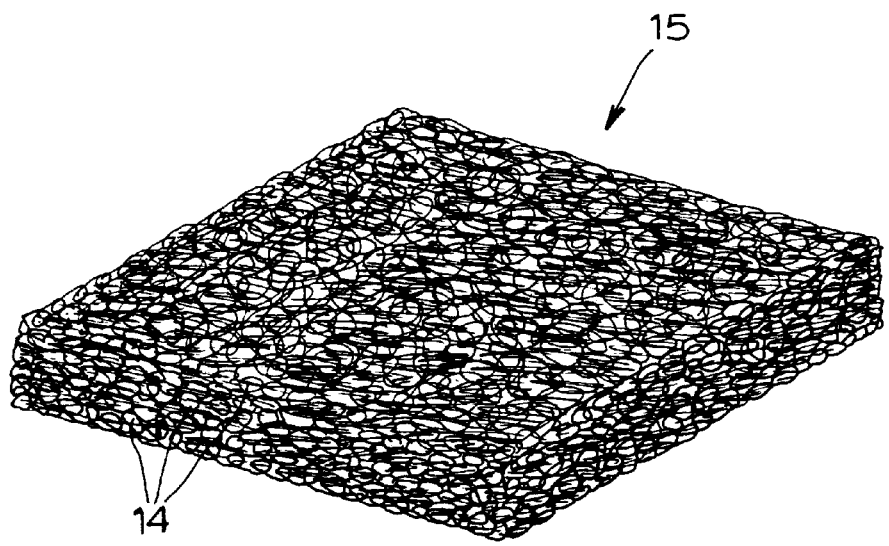

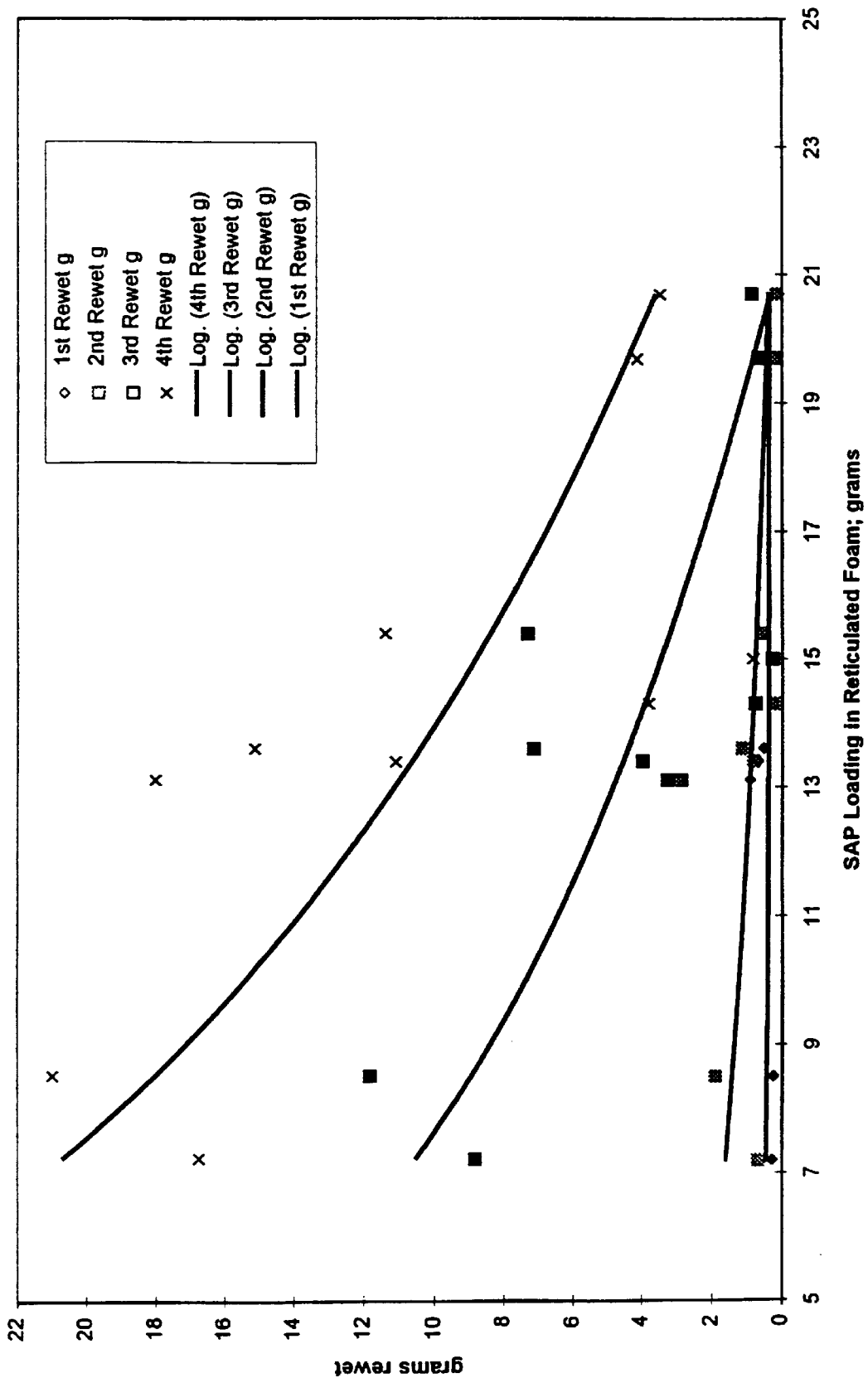

WATER-ABSORBENT ARTICLE AND METHOD

FIELD OF THE INVENTION

The present invention is directed to an absorbent article that incorporates a superabsorbent material, such as partially neutralized polyacrylic acid, adhered to a support structure. The support structure includes spaced filaments or fibers in the form of a netting, mesh or fibrous woven or non-woven webs or open-celled foam structure for maintaining the superabsorbent material sufficiently spaced to avoid gel blocking when the superabsorbent material is wetted and swelled. The absorbent structure comprising support fibers and adhered superabsorbent material can function without water-absorbent fibers, such as cellulosic fibers, or may be used together with absorbent fibers.

BACKGROUND OF THE INVENTION AND PRIOR ART

Superabsorbent polymers have been in use in disposable absorbent articles, such as diapers and bandages for many years. Such superabsorbent polymers are capable of absorbing many times their weight of water and body fluids and can retain such absorbed liquids under moderate pressure, as measured by absorption under load (AUL). These superabsorbent polymers have been used together with a batt of absorbent fibers, such as cellulose fibers, to absorb and hold the liquid within the product. The most common absorbent batt used in the diaper art is manufactured from fluffed wood pulp fibers, as disclosed in U.S. Pat. No. 2,788,003, hereby incorporated by reference. A densified paper-like surface layer also has been used in conjunction with an absorbent batt to improve "wicking" of the liquid to the absorbent batt, as disclosed in U.S. Pat. Nos. 3,612,055 and 3,938,522, both hereby incorporated by reference. The absorbent structure of the present invention is useful with or without the absorbent batt and/or wicking layers disclosed in the above-identified patents.

One of the biggest problems associated with the use of superabsorbent polymers in an absorbent product is that of preventing so called "gel blocking". When liquid contacts a superabsorbent material, the superabsorbent material swells extensively. If superabsorbent particles are held too closely together in the absorbent structure, swelling of one superabsorbent particle inhibits the swelling of an adjacent, contacting superabsorbent particle so that the swelling (gelled) superabsorbent material prevents (blocks) further penetration of the liquid into the structure, thereby preventing all of the available superabsorbent material from being efficiently utilized.

One effort to avoid "gel blocking" is disclosed in the Pieniak, et al. U.S. Pat. No. 4,500,315 wherein particles of superabsorbent material are dispersed randomly throughout an absorbent fibrous web containing absorbent fibers, such as cellulosic fibers and/or peat moss. The absorbent fibrous web is compressed, after incorporating the superabsorbent material, to densify the absorbent web and hold the superabsorbent material in place with adjacent, frictionally entangled contacting absorbent fibers. It is asserted in the Pieniak, et al. patent that the fibrous web sufficiently spaces the superabsorbent particles, and the particles are sufficiently small, such that swelling of one superabsorbent particle does not interfere with the absorption of liquid and swelling of adjacent superabsorbent particles. However, it has been found that due to the random, free positioning of the superabsorbent particles, some of the superabsorbent particles sometimes interfere with absorption and swelling of adjacent superabsorbent particles.

In accordance with the principles of the present invention, superabsorbent particles are fixed to a support structure that has a fixed but flexible configuration so that the superabsorbent particles adhered thereto also have definite, fixed positions, with known spacing between adjacent superabsorbent particles, thereby assuring little or no gel blocking.

SUMMARY OF THE INVENTION

In brief, the present invention is directed to an absorbent article including a flexible, fibrous support structure or framework in a fixed shape or configuration having particles of a superabsorbent material adhered thereto to temperature softened outer support surfaces, or with an elastic adhesive to maintain sufficient spacing between adjacent superabsorbent particles such that liquid can more freely enter the absorbent article for contact with the superabsorbent particles.

Accordingly, one aspect of the present invention is to provide an aqueous liquid absorbent article formed from a fibrous support structure or framework having particles or pieces of a superabsorbent polymer adhered to an outer surface thereof at a weight ration of superabsorbent polymer to fibers above about 2:1 with an adhesive having a percent elongation at break of at least 50% such that the superabsorbent particles or pieces are maintained sufficiently spaced to allow for complete swelling upon hydration.

The above and other aspects and advantages of the present invention will become more apparent from the following detailed description of the preferred embodiments of the present invention, in conjunction with the drawings.

BRIEF DESCRIPTION OF THE DRAWINGS

FIG. 1 is a perspective view of a reticulated polyurethane foam before affixing particles of a superabsorbent polymer (SAP) thereto;

FIG. 2 is a perspective view of the reticulated polyurethane foam of FIG. 1 after adhering superabsorbent particles thereto;

FIG. 9 is a graph that correlates the absorbance of the core structure of FIG. 2 with the amount of SAP adhered to the reticulated polyurethane foam framework or support.

DETAILED DESCRIPTION OF THE PREFERRED EMBODIMENT

Figure 3:
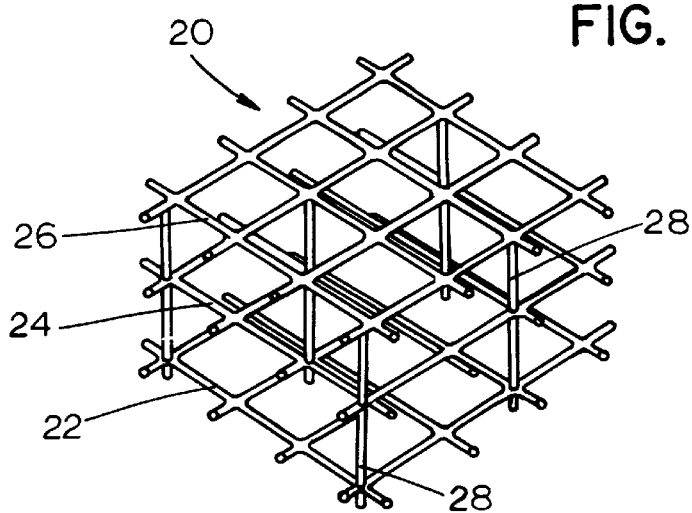
FIGS. 3 and 4 are perspective views of another framework structure showing a monofilament framework structure before SAP loading (FIG. 3) and after SAP loading (FIG. 4)

Referring now to the drawings, FIG. 1 shows a preferred form of a fibrous support structure or framework 10 which is an open-celled reticulated open-pore foam matrix made from polyurethane. The reticulated foam matrix is compressible but capable of springing back to its original volume and configuration, upon release of pressure, to maintain a desired spacing between adjacent superabsorbent particles that are adhesively affixed to the cell structure. Open-cell foam structures are, as defined by the manufacturing process, fixed in size and configuration by virtue of the foam being an integral, structurally fixed mass having a uniform cell size, a substantial volume of void space, up to about 98%, and having surface areas up to about 2,000 ft$^2$ per ft$^3$. Each open cell is integral with adjacent open cells so that the configuration of the material, while being compressible, is fixed, and the structure returns to its original configuration and volume after the release of compressive forces. The average pore size for the open-cell foam material should be greater than the average diameter of the superabsorbent particles adhered thereto to avoid or minimize gel blocking. The preferred material for forming the support matrix 10 is a reticulated polyurethane foam, such as FILTERCREST polyurethane foam from Crest Foam Industries, Inc., Moonachie, N.J., available from about 4 pores per inch to about 90 pores per inch, e.g., 4 pores per inch to 90 pores per inch. However, other support materials also are useful, such as non-reticulated foams polymeric materials, e.g..; polyethylene, polypropylene, nylon, polyester and polyether materials in monofilaments, woven or non-woven fabrics; cotton thread; non-woven fabrics; tissue paper, and the like.

A preferred embodiment of the support structure 10 is preferably a large-pore reticulated polyurethane foam with a liter volume weight of 20 to 60 grams and pores with a diameter about 0.5 mm to about 20 mm, e.g., of 0.5 to 20 mm. Such foams are produced in a known manner by first evacuating a large open-pore foam block located in a closed chamber. Then an explosive gas mixture is allowed to flow into the closed chamber and is then ignited. The cell walls are destroyed by the explosion and melt to form stays or structural supports. Therefore, reticulated foams do not have walls, but rather consist of a grid of stays, which form cages with a diameter of about 1 to about 5 mm. These "foams" are elastic, can be easily compressed by hand, even at a thickness of several centimeters, and then resume their original shape. When the foam walls are completely covered with superabsorbent material particles, as shown in FIG. 2, they are relatively rigid and can no longer be compressed with the same amount of force. Suitable particle sizes for the superabsorbent particle are in the range of about 5 microns to about 1,000 microns, preferably about 150 microns to about 700 microns.

The open-pore structure permits the cell walls to be coated with superabsorbent polymer particles around their entire outer periphery. It is also possible to subsequently cut up these structures to form smaller articles in the form of strips or chips, with a size appropriate for mixing with fluffed wood pulp or other absorbent fibers. The subdivision of the foams into smaller pieces results in complete independence from the shape of the objects to be filled.

The highly air-permeable three-dimensional carrier frameworks of reticulated foams are essentially stable in shape on the basis of the thickness or the strength of monofilaments or fibers of which they are composed, i.e., they should not simply collapse, but are elastic, so that they can be compressed to a certain extent, but then resume their original shape. When the superabsorbent polymer (SAP) particles are affixed to the fibers (cell walls), and these carrier frameworks are preferably completely covered around their entire outer surface area with the superabsorbent particles, the rigidity is increased and the filled carrier frameworks then are relatively rigid, pressure-resistant structures.

Depending on the material of which the carrier framework is formed, the SAP particles can be affixed to it directly, or an adhesive mass is required. Plastic materials, particularly fiber materials, are commercially available which have the property of first becoming sticky on the surface at an elevated temperature, within a certain temperature range, without melting. This property, which could be designated as a built-in hot-melt glue, can be utilized to affix the superabsorbent particles to the carrier framework. Such fibers can be heterophilic fibers made of two coaxially arranged components, the outer one of which demonstrates a lower melting point. Unstretched amorphous polyester fibers which become soft and sticky at approximately 80° C. to 85° C., without melting, and subsequently crystallize at higher temperatures and then have the thermal stability of a normal polyester fiber, are also suitable. Such fibers with adsorbents affixed to them are described for textile surface filters, for example in U.S. Pat. No. 4,983,192, hereby incorporated by reference.

Figure 4:
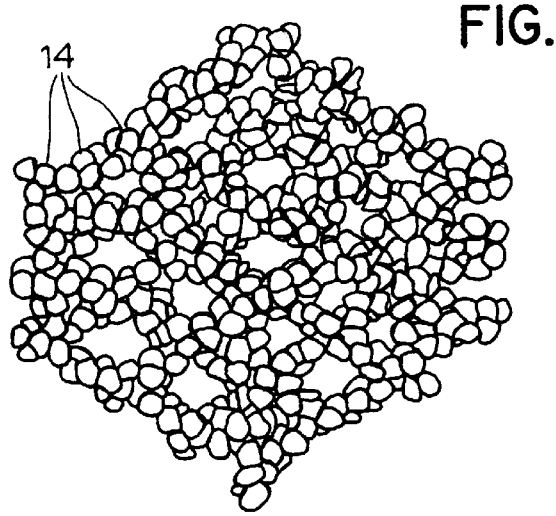
Figure 6:
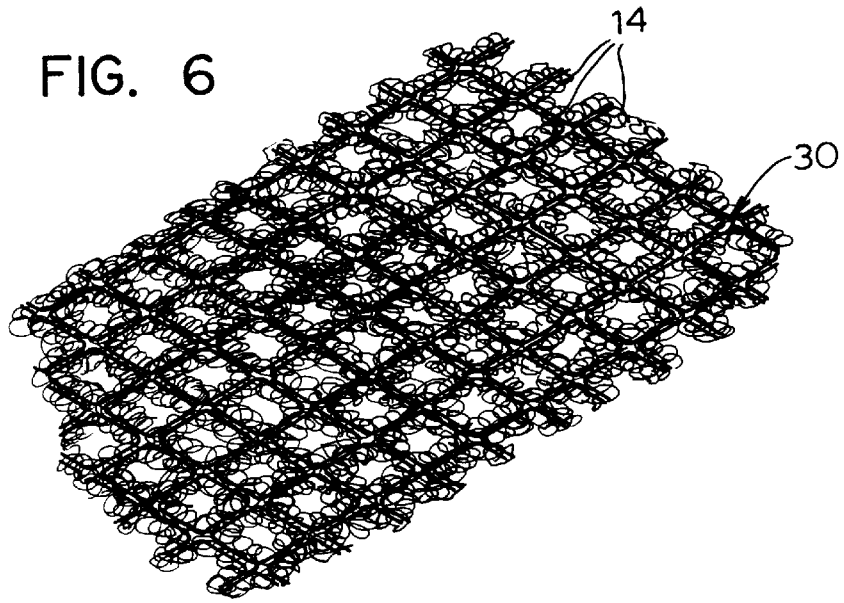

Another expedient preferred for the purposes of the present invention is to affix the superabsorbent particles to the carrier framework with an adhesive mass, as shown in FIGS. 2, 4 and 6. With this alternative, a person skilled in the art has a greater choice of carrier framework material, as well as many choices for the particular adhesive.

The superabsorbent material is generally a water-insoluble but water-swellable polymeric material capable of absorbing water in an amount which is at least 10 times the weight of the material in its dry form. The superabsorbent material is in the form of particles, powders, granules, film pieces or the like which may be in the shape of fibers, spheres, bits of film, or the like, or may be applied to the support structure in the form of a partially cured polymer, or as a coating of liquid monomer which is subsequently polymerized. Generally, the polymerized liquid monomer provides particles and bits of film-like superabsorbent particles attached to the carrier framework structure.

The particles, fibers or film pieces may be described chemically as having a polymeric backbone with hydrophilic groups, or polymers containing hydrophilic groups chemically bonded to the polymer backbone. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to enhance their water absorbance and render them water-insoluble.

These same superabsorbent polymers, such as polysaccharides, may also serve, for example, as the backbone onto which other polymer moieties may be bonded by graft copolymerization techniques. Such grafted polysaccharides and their method of manufacture are described in U.S. Pat. No. 4,105,033 to Chatterjee et al., hereby incorporated by reference.

In addition to modified natural and regenerated polymers, the superabsorbent, e.g., hydrocolloid, particle component may comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly(alkyl phosphonates), partially hydrolyzed polyacrylamides (e.g., poly(n-N-dimethyl acrylamide), sulfonated polystyrene, or poly (alkylene oxide). These highly hydrophilic synthetic polymers may be modified by other chemical treatments such as cross-linking or hydrolysis. Further examples known in the art are the non-ionic hydrophilic polymers such as polyoxyethylene, polyoxypropylene and mixtures thereof which have been suitably cross-linked, either chemically or with radiation. Still another type is a derivative of isobutylene-maleic anhydride copolymer.

Partially cross-linked hydrophilic polymers formed from water-soluble acrylate monomers, such as sodium, potassium, ammonium (or combination of cations) acrylate, 50–100 mole percent neutralized, preferably 70–80 mole percent neutralized, are the preferred superabsorbent materials and may be used as particles of the superabsorbent material, or as a coating of monomer solution followed by polymerization and cross-linking, for example, by irradiation, in situ, coated onto the support structure.

Any superabsorbent material which absorbs large amounts of aqueous liquids is suitable for use as the superabsorbent material of the present invention. Partially neutralized acrylic acid (e.g., 70–75 mole percent neutralized) is the preferred superabsorbent polymer material.

The superabsorbent material is adhered to the support structure either by coating the polymer over the support structure, or by adhering superabsorbent particles to the support structure having a softened, adhesive outer surface, or by adhering the polymer with a suitable adhesive. If a relatively low loading of superabsorbent particles is applied to the support structure with an adhesive, e.g., at a weight ratio of superabsorbent particles to support structure below about 1:1, such that the superabsorbent particles, when hydrated, do not pressure adjacent particles, e.g., for use as a desiccant, e.g., gas dehydrating, the adhesive can be rigid and non-elastic. At a weight ratio of superabsorbent to support structure above about 2:1, the adhesive should be somewhat elastic, having a percent elongation at break of at least about 50%, preferably at least about 100%, e.g. 100% more preferably at least about 500%, e.g. 500% to maintain the adherence of the superabsorbent particles to the support structure even after the particles are completely hydrated and completely swelled. Suitable adhesives include Bayhydrol DLN (Bayer) and Tycel 7000 (Liofol Company). Bayhydrol DLN is an aliphatic polyester polyurethane resin having a percent elongation at break of 600%, when air dried at 75° F. and 55% relative humidity and then baked for 10 minutes at 300° F., and is available at 40% by weight concentration, in water. Tycel 7000 also is a polyurethane adhesive available in a choice of solvents for varied drying times, and has a percent elongation at break of 100–200%.

The superabsorbent particles should not be completely coated with the adhesive so that aqueous liquids can penetrate the uncoated portion of the superabsorbent particles sufficiently for aqueous liquid absorption. The preferred method of affixing the superabsorbent particles to the support structure is to dip the support structure into the liquid adhesive, thereafter shaking the support structure to remove excess adhesive, and then sprinkling superabsorbent particles onto the wet, adhesive-coated support structure until the support matrix is completely covered with superabsorbent particles. The structure then is placed into an oven or otherwise heated to the adhesive curing temperature to permanently affix the superabsorbent particles to the support structure. In this manner, the elastomeric adhesive establishes "point contact" with the reticulated foam matrix. This point contact allows the superabsorbent particles to swell in aqueous fluids to at least 10 times their original volume while remaining attached to the reticulated cell support structure. The elastomeric quality of the adhesive allows it to elongate without breaking as the superabsorbent particles swell while in contact with adjacent superabsorbent particles, so that the particles can move away from the support structure while gaining volume, thereby maintaining adherence to the support structure while the adhesive stretches. As a result, the majority of the superabsorbent particles remain attached to the support structure despite the substantial swelling of the hydrated superabsorbent particles, and increased spacing of the particles from the support structure.

Turning now to the drawings and initially to FIG. 1, FIG. 1 shows a reticulated polyurethane foam material 10 having open cell walls 12. As shown in FIG. 2, the foam material 10 is coated with superabsorbent particles 14 to form absorbent article 15 by dipping the foam material 10 into a suitable adhesive, shaking off any excess adhesive, and then sprinkling the superabsorbent particles onto the adhesive-coated foam material 10.

Turning now to FIGS. 3 and 4, other forms of the support structure are shown for supporting coated or adhesively affixed superabsorbent polymer material. As shown in FIG. 3, the support structure 20 is in the form of a plurality of vertically spaced polymeric netting or polymeric mesh structures 22, 24 and 26, such as polyethylene or polypropylene monofilaments, having a mesh width of about 0.5 mm to about 20 mm, superimposed in parallel planes, in layers, and having vertical spacer filaments 28 disposed between and integral with the vertically spaced netting structures 22, 24 and 26 to maintain a desired vertical spacing of about 0.5 mm to about 20 mm. FIG. 4 shows the support structure of FIG. 3 having particles 14 of superabsorbent polymer melt affixed, or adhesively affixed to the netting structures 22, 24, 26, and vertical spacer filaments 28.

Figure 5:
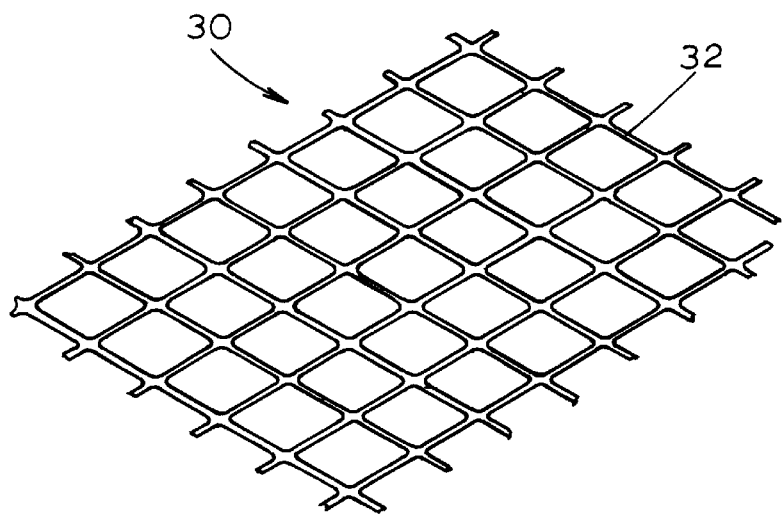
FIGS. 5 and 6 are perspective views of a netting monofilament framework structure before SAP loading (FIG. 5) and after SAP loading (FIG. 6)
Figure 7:
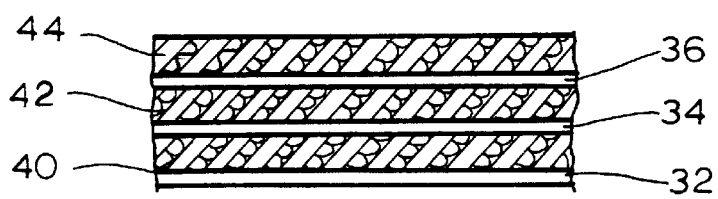
FIG. 7 is a side view of a portion of another embodiment of the present invention, showing three SAP-filled netting structures of FIG. 6 separated by fluffed wood pulp absorbent batts (40, 42 and 44)

As shown in FIGS. 5–7, a single netting structure 30 is also useful after affixing superabsorbent particles or pieces 14 to the polymeric, e.g., polyethylene monofilament, structure 30 having open pores between monofilaments with an average pore opening size in the range of about 0.1 mm to about 50 mm. A single netting structure 32 can be used alone as shown in FIG. 6, or a netting structure 32 can be vertically spaced from identical or similar netting structures 34, 36 by layers of hydrophilic fibers 40, 42, 44 consisting essentially of cellulosic fibers, e.g., fluffed wood pulp and/or denser paper-like wicking sheets, as shown in FIG. 7.

Figure 8:
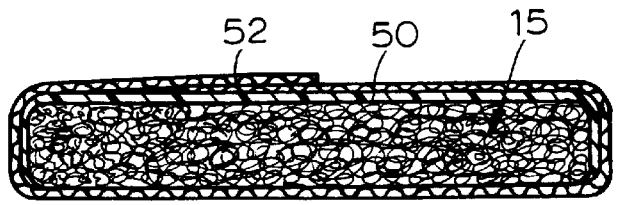
FIG. 8 is a cross-sectional view of the absorbent article of FIG. 2 encased within a water-permeable cellulosic cover layer to hold the superabsorbent particles captive, in the event that superabsorbent particles separate from the framework or support structure during use.

As well known in the art of diaper construction, as shown in FIG. 8, the absorbent articles shown in FIGS. 2, 4, 6 and 7 can be contained or encased within cover material, such as a water-impervious (water-impermeable) backing sheet 50 and a water-permeable encasing sheet 52 completely encasing the water- absorbent core 15 and backing sheet 50 and disposed adjacent the user for absorption of body fluids. In this manner, the absorbent structures described herein are used as absorbent cores, as well known in the diaper art.

EXAMPLES

Reticulated polyurethane foam (Crest Foam Industries S-20C) was cut into rectangles 20.5 centimeters by 11.5 centimeters by 0.5 centimeters. The foam was weighed, dipped into Bayhydrol DLN adhesive and then shaken to remove excess adhesive. SAP (70 mole percent neutralized polyacrylic acid) granules were then sprinkled onto the foam to cover the matrix. The composite was then placed in an oven at 105° C. for one hour to cure the adhesive. The composite was removed from the oven and shaken to removed unattached SAP. The composite was then weighed to determine polymer loading (a control was prepared to determine the weight of glue on the foam). The absorbent cores then were tested for absorbency using standard rewet testing, with the results shown in the data of Table 1, plotted in graph form in FIG. 9.

Standard Rewet Testing Procedure

1. Primary Rewet Test
   (a) Place hygienic article flat on bench top by removing elastics and/or taping ends of article to bench.
   (b) Using a separatory funnel, dose the suspected target zone of the article with 100 ml of 1% NaCl solution at a rate of 7 ml/sec. Allow the article to swell for 10 minutes.
   (c) Weigh a stack of 10 Whatman #41 filter papers and record the dry weight. Place the stack of filter papers onto the insult zone. Place a 2.5 kg weight on the filter papers.
   (d) After 2 minutes, remove the weight and weigh the filter papers and record the wet weight.
2. Secondary Rewet Test
   (a) Place a PVC ring over the primary insult zone.
   (b) Repeat steps 1(b)–(d) using 50 ml of 1% NaCl solution and 20 filter papers.
3. Tertiary Rewet Test
   (a) Place the PVC ring over the primary insult zone.
   (b) Repeat steps 1(b)–(d) using 50 ml of 1% NaCl solution and 30 filter papers.
4. Calculation
   Rewet value (g)=wet filter papers weight (g)–dry filter papers weight (g).

TABLE 1

Data From Rewet Studies of SAP Adhered To Reticulated Polyurethane Foam

| Sample | Wt. of Foam | SAP Load g | 1st Rewet g | 2nd Rewet g | 3rd Rewet g | 4th Rewet g |
| --- | --- | --- | --- | --- | --- | --- |
| A | 3.3 | 20.7 | 0.06 | 0.13 | 0.82 | 3.43 |
| B | 3.3 | 19.7 | 0.1 | 0.16 | 0.64 | 4.07 |
| C | 3.3 | 13.1 | 0.87 | 2.85 | 3.25 | 18.01 |
| D | 3.2 | 15.4 | 0.6 | 0.52 | 7.29 | 11.37 |
| E | 3.5 | 7.2 | 0.24 | 0.65 | 8.81 | 16.74 |
| F | 3.4 | 8.5 | 0.2 | 1.88 | 11.81 | 20.98 |
| G | 3.2 | 13.4 | 0.65 | 0.78 | 3.95 | 11.07 |
| H | 3.2 | 13.6 | 0.48 | 1.11 | 7.12 | 15.11 |
| I | 3.8 | 14.3 | 0.22 | 0.23 | 0.73 | 3.78 |
| J | 3.7 | 15 | 0.23 | 0.25 | 0.24 | 0.8 |
| Control | 0 | 6 | 0.1 | 0.7 | 18.1 | — |

The data in Table 1 show that the invention produces absorbent cores with a high degree of core integrity that is superior to conventional core designs. Excellent results are obtained at a weight ratio of superabsorbent to support structure of at least about 2:1; particularly at a weight ratio of superabsorbent to support structure of at least about 4:1; especially within the weight ratio range of about 4:1 to about 10:1 superabsorbent to support structure.

What is claimed is:

1. An aqueous liquid absorbent article comprising a support structure including a framework of spaced fibers having a superabsorbent polymer adhered to outer surfaces of said fibers by adhesively securing the superabsorbent polymer to the fibers, at a weight ratio of superabsorbent polymer to fibers above about 2:1 with an adhesive having a percent elongation at break of at least about 50%, without completely coating the superabsorbent polymer with said adhesive.

2. The article of claim 1, wherein the framework of spaced fibers comprises a plurality of horizontal parallel polymeric fiber netting structures integral with and spaced by vertical polymeric fiber supporting filaments.

3. The article of claim 1, wherein the framework of spaced fibers comprises a polymeric fabric selected from the group consisting of a woven fabric, and a non-woven fabric.

4. The article of claim 1, wherein the framework of spaced fibers comprises a netting structure formed from polymeric monofilaments and having open pores between monofilaments with an average pore opening size in the range of about 0.1 mm to about 50 mm.

5. The article of claim 1, wherein the adhesive has a percent elongation at break of at least about 100%.

6. The article of claim 5, wherein the adhesive has a percent elongation at break of at least about 500%.

7. The article of claim 1, further including a layer of hydrophilic fibers in contact with and coextensive with said support structure.

8. The article of claim 7, wherein said layer of hydrophilic fibers consists essentially of cellulosic fibers.

9. The article of claim 8, wherein said wood pulp fibers comprise fluffed wood pulp fibers.

10. The article of claim 7 further including a second layer of hydrophilic fibers in contact with and coextensive with said support structure and sandwiching said support structure between said two layers of hydrophilic fibers.

11. A product comprising the article of claim 1, and further including a water-impermeable layer covering one major outer surface of the article, and a water-permeable cover layer encasing the article and water-impermeable layer.

12. A method of protecting an area from being wetted by a water source comprising disposing the product of claim 11 between the area to be protected and said water source such that the water-impermeable layer is facing the area to be protected.

13. The article of claim 1, wherein the weight ratio of superabsorbent polymer to fibers is at least about 4:1.

14. The article of claim 13, wherein the weight ratio of superabsorbent polymer to fibers is in the range of about 4:1 to about 10:1.

15. An aqueous liquid absorbent article comprising a support structure consisting essentially of an open-celled reticulated polyurethane foam material comprising a plurality of integral cell structures having a superabsorbent polymer adhesively secured to outer surfaces of the cell structures by adhesively securing the superabsorbent polymer to the cell structures, at a weight ratio of super absorbent polymer to open-celled reticulated polyurethane foam material above about 2:1 with an adhesive having a percent elongation at break of at least about 50%, without completely coating the superabsorbent polymer with said adhesive.

16. The article of claim 15, wherein the reticulated polyurethane foam material has a pore diameter of about 0.5 mm to about 20 mm.

17. The article of claim 15, wherein the foam material has about 4 to about 90 pores per inch.

18. The article of claim 15, wherein open-celled polyurethane foam material comprises cases with diameters in the range of about 1 mm to about 5 mm.

19. The article of claim 15, further including a layer of hydrophilic fibers in contact with and coextensive with said support structure.

20. The article of claim 23, wherein said hydrophilic fibers consist essentially of cellulosic fibers.

21. The article of claim 20, wherein said to cellulosic fibers comprise fluffed wood pulp fibers.

22. The article of claim 19 further including a second layer of hydrophilic fibers in contact with and coextensive with said support structure and sandwiching said support structure between said two layers of hydrophilic fibers.

23. A product comprising the article of claim 15, further including a water-impermeable layer covering one major outer surface of the article, and a water-permeable cover layer encasing the article and water-impermeable layer.

24. A method of protecting an area from being wetted by a water source comprising disposing the product of claim 23 between the area to be protected and said water source such that the water-impermeable layer is facing the area to be protected.

25. The article of claim 15, wherein the weight ratio of superabsorbent polymer to open-celled polyurethane foam material is at least about 4:1.

26. The article of claim 25, wherein the weight ratio of superabsorbent polymer to open-celled polyurethane foam material is in the range of about 4:1 to about 10:1.

* * * * *